(12) United States Patent
Bakker et al.

(10) Patent No.: US 9,080,930 B2
(45) Date of Patent: Jul. 14, 2015

(54) GAS SAMPLING FOR $CO_2$ ASSAY

(75) Inventors: Fredericus Petrus Bakker, Beverwijk (NL); Jacobus Wilhelmus Hooijmans, Schagen (NL); Pieter Sebastiaan Wardenaar, Schagen (NL)

(73) Assignee: Stichting Energieonderzoek Centrum Nederland, Petten (NL)

( * ) Notice: Subject to any disclaimer, the term of this patent is extended or adjusted under 35 U.S.C. 154(b) by 395 days.

(21) Appl. No.: 13/704,224

(22) PCT Filed: Jun. 14, 2011

(86) PCT No.: PCT/NL2011/050426
§ 371 (c)(1),
(2), (4) Date: Feb. 28, 2013

(87) PCT Pub. No.: WO2012/005570
PCT Pub. Date: Jan. 12, 2012

(65) Prior Publication Data
US 2013/0174673 A1      Jul. 11, 2013

(30) Foreign Application Priority Data
Jun. 14, 2010   (NL) .................................... 2004884

(51) Int. Cl.
*G01N 1/22* (2006.01)
*F23G 5/50* (2006.01)
(Continued)

(52) U.S. Cl.
CPC .. *G01N 1/22* (2013.01); *F23G 5/50* (2013.01); *F23N 5/003* (2013.01); *G01N 1/2214* (2013.01);
(Continued)

(58) Field of Classification Search
CPC ...... F23J 15/02; G01N 1/2247; G01N 1/2258
See application file for complete search history.

(56) References Cited

U.S. PATENT DOCUMENTS 4,313,916 A * 2/1982 Jones et al. .................... 423/226
4,407,723 A * 10/1983 MacGregor et al. .......... 252/192
(Continued)

FOREIGN PATENT DOCUMENTS

CH              684610 A5   10/1994
DE       101 59 967 A1    6/2003
(Continued)

OTHER PUBLICATIONS

Siriwardane et al., "Adsorption and Desorption of CO on Solid Sorbents", 2001.*
(Continued)

*Primary Examiner* — David A Rogers
(74) *Attorney, Agent, or Firm* — Gilberto M. Villacorta; Sunit Talapatra; Foley & Lardner LLP (57) ABSTRACT

The invention provides a method for sampling gas in a flue gas stream (31) of an incineration furnace (1) or another $CO_2$-containing gas stream. The method comprises sampling $CO_2$ from the flue gas stream (31) of the incineration furnace (1) and storing $CO_2$ from the flue gas stream (31) in a storage device (5). The storage device comprises a solid, preferably silica- or alumina-based $CO_2$ storage material, which can be regenerated. The method further preferably involves transporting the storage device (5) to an analysis site (10) comprising an apparatus for $^{14}C$ analysis, retrieving at least part of th stored $CO_2$ from the storage device (5) and determining, based on the $^{14}C$ analysis, the ratio of biomass-derived and fossil-derived $CO_2$ in the flue gas stream (31).

8 Claims, 2 Drawing Sheets

(51) Int. Cl.
| | |
|---|---|
| *F23N 5/00* | (2006.01) |
| *B01D 53/62* | (2006.01) |
| *G01N 1/40* | (2006.01) |
| *G01N 31/12* | (2006.01) |
| *G01N 33/22* | (2006.01) |

(52) U.S. Cl.
CPC .............. *G01N 1/2258* (2013.01); *B01D 53/62* (2013.01); *B01D 2257/504* (2013.01); *F23G 2900/55011* (2013.01); *F23N 2021/10* (2013.01); *G01N 1/405* (2013.01); *G01N 31/12* (2013.01); *G01N 33/22* (2013.01); *Y02E 20/328* (2013.01)

(56) References Cited

U.S. PATENT DOCUMENTS

| | | | | |
|---|---|---|---|---|
| 4,619,902 | A * | 10/1986 | Bernard | 436/145 |
| 5,087,597 | A * | 2/1992 | Leal et al. | 502/62 |
| 5,507,848 | A * | 4/1996 | Beckman | 55/522 |
| 6,387,337 | B1 | 5/2002 | Pennline et al. | |
| 7,914,758 | B2 * | 3/2011 | Murray et al. | 423/220 |
| 8,894,747 | B2 * | 11/2014 | Eisenberger et al. | 95/139 |
| 2004/0244507 | A1 * | 12/2004 | Benz | 73/864.81 |
| 2006/0148642 | A1 | 7/2006 | Ryu et al. | |
| 2007/0036683 | A1 | 2/2007 | Hirst | |
| 2007/0149398 | A1 * | 6/2007 | Jones et al. | 502/402 |
| 2008/0031801 | A1 * | 2/2008 | Lackner et al. | 423/438 |
| 2009/0127127 | A1 * | 5/2009 | Jones | 205/464 |
| 2009/0308168 | A1 | 12/2009 | Motoyama | |
| 2010/0132422 | A1 | 6/2010 | Canari | |
| 2012/0118009 | A1 * | 5/2012 | Minhas et al. | 62/617 |
| 2014/0284521 | A1 * | 9/2014 | Deguchi et al. | 252/190 |

FOREIGN PATENT DOCUMENTS

| | | |
|---|---|---|
| EP | 2 009 092 A1 | 12/2008 |
| WO | WO-02/06730 A1 | 1/2002 |
| WO | WO-2009/054718 A1 | 4/2009 |
| WO | WO 2009054718 A1 * | 4/2009 ............ G01N 31/12 |

OTHER PUBLICATIONS

Siriwardane et al., "CO2 Capture Utilizing Solid Sorbents", Fuel Chemistry Division Preprints, 2002.*

International Preliminary Report on Patentability for PCT/NL2011/050426—mailed Oct. 15, 2012.

International Search Report for PCT/NL2011/050426—mailed Oct. 31, 2011.

Staber W et al: "Methods for determining the biomass content of waste", Waste Management and Research, Academic Press, Longon, US, vol. 26, No. 1, Feb. 1, 2008, pp. 78-87, XP009142176.

* cited by examiner

GAS SAMPLING FOR CO₂ ASSAY

CROSS-REFERENCE TO RELATED APPLICATION(S)

This application is the National Phase of International Patent Application No. PCT/NL2011/050426, filed Jun. 14, 2011, published as WO 2012/005570, which claims priority to Netherland Application No. 2004884, filed Jun. 14, 2010. The contents of these applications are herein incorporated by reference in their entirety.

FIELD OF THE INVENTION

The invention relates to a method for sampling of flue gas for determining the ratio of biomass-derived and fossil-derived $CO_2$ in the flue gas stream of an incineration furnace. The invention further relates as to a storage device that can be used in such method.

BACKGROUND OF THE INVENTION

Various kinds of material are fed to incineration furnaces, for the most part fossil fuels, that is to say fuels which are tens of thousands of years old and older. In particular in the case of waste incinerators, but also with other incineration furnaces, a fuel stream may also be supplied which comprises fuels which are less old. Examples thereof are wood, rubber material and the like. These fuels are also referred to as biogenic (or biogen) fuels ("biomass").

For environmental reasons, it is desirable to limit the emission of the greenhouse gas $CO_2$ as much as possible, in particular the $CO_2$ which is generated during the combustion of fossil fuels. Combustion of carbon which has been converted to, for example, wood relatively recently is not considered to be polluting. After all, wood is only a few tens to hundreds of years old and is the result of the conversion of carbon dioxide from the atmosphere to carbon.

In certain countries, levies have even been introduced for the emission of fossil fuel, that is to say fuel which originated more than 10,000 years ago.

If a mixed fuel stream is fed to an incineration furnace, it is important to know which fraction of the supplied fuel is fossil and which fraction of the fuel is more recent.

Fossil and recent (non-fossil) carbon can be distinguished by their $^{14}C$ content. Non-fossil carbon originates from the atmosphere relatively recently, and atmospheric carbon is enriched in $^{14}C$ by cosmic irradiation of $^{14}N$. As a result, atmospheric carbon contains approximately 1 ppt (1 per $10^{12}$) of $^{14}C$ on total carbon.

$^{14}C$ is a radioactive element having a half-life of approximately 5700 years, which means that within said period, half of the $^{14}C$ content of any organic material which does not take part in the carbon cycle will have decayed (back to $^{14}N$). Consequently, essentially all $^{14}C$ will have disappeared within about 60,000 years if the carbon was stored underground. In other words, the $^{14}C$ content of fossil fuels is zero, while in recent biogenic fuels it is essentially the same as it is in the atmospheric carbon (approximately 1 ppt).

The $CO_2$ which is present in a waste gas may partly originate from fossil fuels and partly from biogenic fuels (biomass). By determining the $^{14}C$ content, the amount of fossil and biogenic fuel, respectively, can be known. If the total $CO_2$ percentage is known, the amount of fossil fuel in a sample can be calculated in a simple manner. Using the results, it is possible to determine, for example, charges and the like.

One possibility of determining this is through the analysis of the stream which is supplied. Such a method is inaccurate when only random checks are carried out. In addition, it requires highly experienced investigators and/or is complicated.

WO2002/06730 describes a method for determining the relationship between fossil and non-fossil energy carriers in a fuel mixture by determining the $^{14}C/^{12}C$ and/or $^{3}H/^{1}$.

WO2009/054718 describes a method and device for determining the fossil fuel content in a fuel stream fed to an incineration furnace. The waste gas is sampled in a sampling container, presumably in gas form, and the amount of "new" and "old" carbon present in the $CO_2$ is determined by analysing the level of $^{14}C$ of the $CO_2$ in the sampling container, e.g. using liquid scintillation counting. The handling of the sampled $CO_2$ in gaseous form, however, is cumbersome, especially where the analysis site is at a distance from the sampling site DE 10159967 discloses a method of collecting $^{14}C$ from off-gas of nuclear power plants, by using caustic soda which is absorbed on a supporting web. The amount of absorbed $CO_2$ from the off-gas is used as a measure of the amount of off-gas which has been sampled. and then assaying the level of $^{14}C$ in the collected $CO_2$.

A disadvantage of prior art is that on-line analysis of $^{14}C$ is not possible. This implies a storage of the $CO_2$. It would be possible to store $CO_2$ in a liquid, such as a NaOH solution. A disadvantage however of liquid storage mediums is that they are more difficult to transport and are less robust. Further, the reliability of liquid storage may be less than desired.

SUMMARY OF THE INVENTION

It is an aspect of the invention to provide an alternative sampling method for determining the ratio of biomass-derived and fossil-derived $CO_2$ in a flue gas stream, which obviates one or more of above-described drawbacks.

It is further an aspect of the invention to provide a sampling device arranged to sample $CO_2$ from a flue gas stream of an incineration furnace or form another source, and to an incineration furnace comprising such a sampling device.

It is further an aspect of the invention to provide a storage device for storing the $CO_2$ from a flue gas stream of an incineration furnace.

DESCRIPTION OF THE INVENTION

In a first aspect, the invention provides a method for sampling flue gas for determining the ratio of biomass-derived and fossil-derived $CO_2$ in a flue gas stream of an incineration furnace or another $CO_2$-containing gas stream, the method comprising sampling $CO_2$ from the flue gas stream and storing $CO_2$ from the flue gas stream in a storage device, wherein the storage device comprises a solid based $CO_2$ storage material. The storage material can preferably be regenerated as described below. After sampling, the storage device can be transported to an analysis site comprising an apparatus for $^{14}C$ analysis, where the stored $CO_2$ is retrieved from the storage device and, the ratio of biomass-derived and fossil-derived $CO_2$ in the flue gas stream is determined by $^{14}C$ analysis. Now, the $^{14}C$ analysis may be performed easily and reliably at a site which is remote from the incineration furnace. Hence, the method is especially designed to determine the ratio between biogenic and fossil $CO_2$ in the flue gas. In this way, also the ratio biogenic and fossil carbon, i.e. the ratio of biomass-derived and fossil-derived carbon in the fuel fed to the incineration furnace can be determined.

An advantage of this method is that sampling is easier than when sampling with a liquid. Further, the storage device is less accessible or less open to external influences than a liquid storage device. This may prevent or reduce damage, destruction or fraud of the storage device. It also makes transport easier. Further, the concentration of $CO_2$ in the sample is not influenced by evaporation of the storage medium, as may be the case with a liquid based storage device. Another advantage of the method and apparatus of the invention is that sampling may be proportional to the flue gas flow.

There are various techniques for determining $^{14}C$. An important technique is liquid scintillation counting (LSC), which allows very accurate measurements, for example having a relative standard deviation of less than 1% with samples which contain at least 25% of biogenic mass. However, it is also possible to obtain good results with very low contents of non-fossil fuel, that is to say 5% or less. Other methods for determining $^{14}C$ use beta ionization (BI) gas counters and accelerated mass spectrometry (AMS), which are preferred if high accuracy is required. For determining the total stream of waste gas or flue gas, a mass flow monitor can be used.

The accuracy of the method can be improved if a relationship is established between the sampled amount and the amount of discharged gas. This applies in particular in the case of varying amounts of discharged gas. This relationship is preferably linear, that is to say that the variation in the sampling is directly proportional to the variation in the amount of discharged gas.

Such a proportional mode constitutes a preferred embodiment of the invention. In a proportional sampling method, the amount of flue gas contacted with the storage material is proportional to the flue gas flow. Thus, when the flue gas at a certain point in time during sampling is only a proportion of the maximum flow, the flow of flue gas passing through the storage device and hence the amount of flue gas contacted with the storage material is of the same proportion with respect to the flow and the amount at the maximum flue gas flow. This can be achieved by measuring the flue gas flow and adapting the flow through the storage device accordingly, for example by a continuous, preferably automated measuring system which controls the opening of the storage device.

The invention may in an aspect also be defined as a method for determining the relationship between fossil and non-fossil energy carriers in a fuel (mixture) by determining the ratio of biomass-derived and fossil-derived $CO_2$ in a flue gas stream of an incineration furnace wherein the fuel (mixture) is combusted, the method comprising sampling $CO_2$ from the flue gas stream of the incineration furnace and storing $CO_2$ from the flue gas stream in a storage device, wherein the storage device comprises a solid based $CO_2$ storage material, transporting the storage device to an analysis site comprising an apparatus for $^{14}C$ analysis, retrieving at least part of the stored $CO_2$ from the storage device and determining, based on the $^{14}C$ analysis, the ratio of biomass-derived and fossil-derived $CO_2$ in the flue gas stream. Hence, the fossil fuel content in a fuel fed to an incineration furnace is determined.

The invention may in an aspect also be defined as a method for determining the relative amounts of biomass-derived and fossil-derived $CO_2$ in a flue gas stream of an incineration furnace, the method comprising sampling $CO_2$ from the flue gas stream of the incineration furnace and storing $CO_2$ from the flue gas stream in a storage device, wherein the storage device comprises a solid based $CO_2$ storage material, transporting the storage device to an analysis site comprising an apparatus for $^{14}C$ analysis, retrieving at least part of the stored $CO_2$ from the storage device and determining, based on the $^{14}C$ analysis, the relative amounts of biomass-derived and fossil-derived $CO_2$ in the flue gas stream.

The fuel fed to the incineration furnace may comprise fossil fuel and non-fossil fuel. Examples of this non-fossil or biogenic fuel are wood, packaging materials, paper, household vegetable waste, manure, slaughter waste, certain kinds of plastics, (car) tyres and the like. Examples of fossil fuel are natural gas, (crude oil based) diesel, and crude or refined oils, tar, bitumen, coal, etc.

The incineration furnace may, for example, comprise the furnace of a household waste incineration furnace. Other applications, such as in the production of cement and in power plants, are also possible. Preferably, the incineration furnace is of the type which can be fed with flue gas streams of varying composition. Examples are household waste incineration furnaces and furnaces which are used in calcination, for example for preparing cement.

The incineration furnace may in an embodiment comprise an inlet for a fuel, an outlet for the discharge of flue gas, and a sampling device. The sampling device preferably comprises a sampling device inlet which can be connected to the furnace outlet for receiving at least part of the flue gas. The sampling device is preferably provided with a valve for the sampling device inlet and a valve control. Further, a sensor may be provided in the incineration furnace outlet which may be connected to the valve control for determining the total amount of flue gas. The valve control is especially arranged to control the size of the valve opening to the sampling device inlet depending on the total flue gas stream which has been measured by the sensor. Further, the sampling device comprises a removable storage device, for storing $CO_2$ from the flue gas stream. Hence, at least part of the waste gas is sampled and fed to the storage device. The storage device stores the $CO_2$.

The term "flue gas" especially refers to a gas that exits in general to the atmosphere via a flue, which is a pipe or channel for conveying exhaust gases from a fireplace, oven, furnace, boiler or steam generator ("incineration furnaces"). Often, it refers to the combustion exhaust gas produced at power plants. The flue gas may comprise a waste gas, especially when it is only fed to an exhaust. Also, the gas stream may originate from a municipal waste incinerator, thus allowing the determination of the proportion of biomass-derived waste. Similarly, the gas stream may issue from a papermaking industry for determining the proportion of wood-derived paper, or from the cement industry. The flue gas may also comprise a process gas, for instance when the gas is (re)used in part of a process.

Storage may be absorption based, such as for instance via a chemical reaction with for instance NaOH, or preferably via strong adsorption, such as with a hydrotalcite (see also below).

The storage device comprises a solid $CO_2$ storage material. The nature and the amount of storage material must be such to allow capture of all $CO_2$ from the gas contacted with the material during the sampling period. This capture must be essentially irreversible under the sampling conditions. The storage material must also allow the complete removal of the stored $CO_2$ for the purpose of the $^{14}C$ measurement. Complete removal of $CO_2$ from the storage material can be achieved e.g. by complete dissolution of the material and subsequent measurement of the $CO_2$ in or from the solution. Alternatively, complete removal of $CO_2$ from the storage material can be achieved in a reversible manner, for example by applying heat.

The storage material preferably contains a primary $CO_2$ absorbent such as a metal hydroxide or an amine, and a secondary material, such as alumina and/or silica, either as a carrier or integrated with the further components of the storage material. The relative amount of secondary material such as alumina and/or silica is preferably at least 10 wt. % of the (dry, unloaded) storage material, up to e.g. 80 wt. % or even 90 wt. %. Storage materials according to the invention containing alumina or silica in any form are referred to herein as alumina-based, or silica-based, respectively. The storage material, with or without a secondary material can conveniently be supported by a structural support, such as metal wire or gauze, an inert synthetic material such as polymer films, glass wool or rock wool etc.

An example of suitable storage materials which can be dissolved for removal of the captured includes a solid alkaline or earth alkaline carbonate precursor, such as a solid metal hydroxide, for example NaOH. The term precursor here refers to a material that may react with $CO_2$ and thereby form a carbonate. Examples thereof are for instance NaOH or KOH, that may react to $Na_2CO_3$ and $K_2CO_3$, respectively. The metal hydroxides may advantageously be present on a carrier material, such as silica or alumina, for example NaOH/$SiO_2$, commercially available e.g. under the trade name Ascarite. The dissolution can be performed in a manner known per se, for example by dissolution in an aqueous mineral acid.

Examples of solid $CO_2$ storage materials capable of reversibly releasing $CO_2$ include (poly)amines, preferably on carrier materials such as silica or alumina, and furthermore hydrotalcites, such as alkaline or earth alkaline loaded hydrotalcites, such as for instance described in US2004/081614, or another alkali-promoted alumina. The latter storage materials are referred to herein collectively as alumina-based materials In a specific embodiment, the solid based $CO_2$ storage material comprises one or more alkali-promoted aluminas, wherein alkali is an element selected from K, Na, Li, Cs, and Rb. Especially, the alkali content is ≥5 wt. % calculated as carbonate, preferably 5-30 wt. % calculated as carbonate, relative to the total amount of the alkali promoted alumina.

Especially, the solid based $CO_2$ storage material comprises one or more alkali-promoted hydrotalcites. Hydrotalcites as used herein are layered mixed oxides and hydroxides of aluminium and magnesium, wherein part of the aluminium may be replaced by other trivalent metals, and the magnesium may be wholly or partly replaced by other divalent metals. In addition to oxides and hydroxides, the hydrotalcites typically contain carbonate and possibly other anions, as well as varying levels of bound water. The hydrotalcite (herein also indicated as "HTC") preferably has the chemical formula:

$$[M^{II}_{(1-x)}Al_{(\alpha x)}M^{III}_{((1-\alpha)x)}(OH)_2][C^{n-}]_{(x/n)}\cdot yH_2O.$$
$$zM^{I}_{(m)}A^{m-}$$

wherein

$M^I$ is one or more of Li, Na, K, Rb and Cs;
$M^{II}$ is one or more of Mg, Ca, Sr, Ba, Ni, Zn, $Mn^{II}$, Cu, Co, $Fe^{II}$, Cd and $Cr^{II}$;
Al is aluminium;
$M^{III}$ is one or more of $Fe^{III}$, $Cr^{III}$ and $Mn^{III}$;
$C^{n-}$ is one or more anions selected from $NO_3^-$, $SO_4^{2-}$, $CO_3^{2-}$, $CH_3CO_2^-$, $Cl^-$, $Br^-$, $F^-$ and $I^-$;
$A^{m-}$ is one or more anions, such as selected from $CO_3^{2-}$, $C_2O_4^{2-}$, $NO_3^-$, $SO_4^{2-}$, $CO_3^{2-}$, $CH_3CO_2^-$, $OH^-$, $Cl^-$, $Br^-$, $F^-$ and $I^-$.
n=1 or 2; x=0.01-0.99; y=0-4; z=0.001-7; and α=0.5-1.

Preferably, the alkali promoter is an element selected from K, Na, Li, Cs, and Rb. Especially, the alkali promoter content is ≥5 wt. % calculated as carbonate, preferably 5-30 wt. % calculated as carbonate, relative to the total amount of the alkali-promoted hydrotalcite. The value of z (i.e. the molar ratio alkali metal to the remaining metals $M^{II}+Al+M^{III}$) is preferably at least about 0.033, more preferably at least 0.1 and in another embodiment preferably not more than about 1.0, more preferably not more than 0.33, in particular up to or about 0.17.

Especially, the solid-based $CO_2$ storage material may comprise an alkali-promoted hydrotalcite, such as potassium-promoted hydrotalcite. Hydrotalcite may for instance be promoted with $K_2CO_3$. In such embodiment, $K_2CO_3$ is applied as source of promoter material to promote the hydrotalcite.

Preferably, the molar ratio $M^{II}:(Al+M^{III})$ (=(1−x):x) is in the range of about 10:90-90:10, preferably 30:70-70:30. The actual oxidation state of some of the $M^{II}$ and ions can be changed during operation, e.g. $Fe^{II}$ and $Fe^{III}$ exist. Further, Al can be the only element present with 3+ oxidation state (α=1). Further, the elements with a 3+ oxidation state can be a mixture of $Al^{3+}$ and $M^{III}$, such as $Fe^{III}$, $Cr^{III}$, and $Mn^{III}$. The molar ratio of $Al^{3+}:M^{3+}$ is preferably 1:1-1:0 (i.e. 0.5≤α≤1).

It surprisingly appears that relatively low x values are especially advantageous. Especially in view of stability, x is in the range of 0.33-0.55. Alternatively, the hydro-talcite material is low in magnesium, i.e. x is in the range of 0.55-0.90.

Especially preferred systems are $Mg_{1-x}Al_{(x)}(OH)_2$  $(CO_3)_{x/2}\cdot z[K_2CO_3]$, wherein x and z have the above indicated ranges (α is in this embodiment 1).

Herein, hydrotalcite may be indicated as an alumina-based material. $M^I$ can be considered as first promoter and $M^{II}$ and $M^{III}$ can be considered as second promoter.

Therefore, an alumina-based solid material, especially a promoted alumina based material may be used as solid based $CO_2$ storage material according to the invention. The promoter(s) may be selected from the group consisting of K, Na, Li, Cs, Rb, Mg, Mn, Ti, Ag, Cu, Co, Pb, Fe and Cd. More than one type of promoter may be applied. Especially, the solid based $CO_2$ storage material comprises a promoted alkali promoted alumina based material, wherein the alumina based material is promoted with one or more first promoters selected from the group consisting of K, Na, Li, Cs, and Rb, and one or more second promoters selected from the group consisting of Mg, Mn, Ti, Ag, Cu, Co, Pb, Fe and Cd. It appears that the second promoter advantageously (further) promotes $CO_2$ capture by the solid based $CO_2$ storage material. Alternatively or additionally, the solid based $CO_2$ storage material comprises the alkali promoted hydrotalcite, as defined above.

An advantage of hydrotalcite materials over aluminas is that it appears that the regeneration of the HTC materials seems easier. Hence, HTC materials may have a longer lifetime and/or be cheaper in maintenance costs.

The phrase "one or more alkali-promoted aluminas" (or alumina-based material) (thus) indicates that in an embodiment a mixture of differently promoted aluminas etc. may be applied. The phrase "wherein alkali is an element selected from the group consisting of K, Na, Li, Cs, and Rb" indicates that the alumina etc. may be promoted with one or more types of alkali metals. Likewise, this applies to promoted alkali-promoted aluminas etc. Further, the phrase "promoted with one or more elements selected from the group consisting of Mg, Mn, Ti, Ag, Cu, Co, Pb, Fe and Cd", and similar phrases, indicates that the (promoted) alumina etc. may be promoted with one or more types of these elements. Preferably, one or more of Mg, Fe and Mn are used as promoter (i.e. second promoter). Preferably, Fe is used as promoter (i.e. second promoter). More preferably, Mg, and Mn are used as promoter (i.e. second promoter), yet even more preferably, Mg.

The terms "alkali-promoted alumina", "promoted alkali-promoted alumina", and "alkali-promoted hydrotalcite" may also include a thermally treated alkali-promoted alumina, thermally treated promoted alkali-promoted alumina, and thermally treated alkali-promoted hydrotalcite, respectively. The thermal treatment may be performed before use as solid $CO_2$ storage material or under the reaction conditions to perform the method of the invention (see also below).

Examples of promoted alumina based materials are for instance selected from $K-Al_2O_3$, $Cs-Al_2O_3$, $K-MgO-Al_2O_3$, $Li-MgO-Al_2O_3$, $K-MnO-Al_2O_3$, $K-Fe-Al_2O_3$ Li—HTC, K—(Mn—Al)HTC, K—(Fe—Al)HTC (with HTC being hydrotalcite). The (alkali-promoted) alumina-based storage materials are suitable for reversible absorption and release of $CO_2$, especially by heating to 200-500° C.

The $CO_2$ release can e.g. be achieved by using a flow of nitrogen or steam, or preferably a mixture thereof containing at least 10% steam. Alternatively, the $CO_2$ release can be effected by using the flue gas itself, especially when the sampling time has been relatively long. The error introduced by the presence of $CO_2$ in this regeneration gas is negligible in view of the relatively short regeneration time, and this embodiment allow a more simple set-up. In this latter embodiment, the storage device need not be transported to the analysis site, and instead, the desorbed $CO_2$ can be collected in a container and be transported to the analysis site, or be analysed in situ.

Thus, the method of the invention can be further characterised by comprising the step of regenerating the storage device, after the sampling period, by heating the storage device to a temperature which allows release of $CO_2$ from the storage material and passing a gas containing nitrogen or water (steam), and preferably not containing $CO_2$, through the storage device. Alternatively, the method of the invention can be characterised by a similar regeneration step comprising passing gas from the same gas stream as the sample gas, i.e. the flue gas stream, while heating.

In another embodiment, the solid based $CO_2$ storage material comprises one or more materials selected from the group consisting of NaOH, KOH, LiOH, $Mg(OH)_2$, $Ca(OH)_2$, $Sr(OH)_2$, and $Ba(OH)_2$, as such or on a carrier material as described above.

Hence, the invention also provides a method, wherein the solid based $CO_2$ storage material comprises a solid alkaline or alkaline earth metal carbonate precursor, and in an embodiment, solid NaOH.

Alternatively or additionally, the solid based $CO_2$ storage material comprises one or more materials selected from the group consisting of amines, such as monoethanol-amine (MEA), diethanolamine (DEA), methyldiethanolamine (MDEA), diisopropyl-amine (DIPA) and aminoethoxyethanol (DGA, diglycolamine). Also, polyamines, such as polyethylenimines (PEI) can be used. The amines are preferably used on a solid secondary material such as silica or alumina carriers, and are suitable for reversible absorption and removal of $CO_2$ A particularly useful amine-based storage material is PEI on $SiO_2$, which can release the $CO_2$ at e.g. 100-150° C. using a nitrogen flow.

Preferably, the sampling device comprises a sealable inlet for the storage device. The sealable inlet may be provided in the sampling device or in the storage device or both. The storage device also has an outlet allowing non-absorbed gas to leave the storage device. The outlet is preferably also sealable and placed at the opposite side of the storage device. This may further add to the reliability of the method. Hence, in an embodiment, the method further includes using a sampling device with a sealable inlet for the storage device. In a specific embodiment, the storage device is a cartridge. This may especially facilitate arrangement and removal of the storage device. Here, the inlet refers to the opening in the sampling device arranged to have the storage device introduced into or connected to the sampling device for receiving the sampled flue gas. Hence, the storage device may be introduced in or connected to the sampling device via the inlet, and this inlet may be sealable. Preferably, the storage device is introduced into the sampling device, like a cartridge, and after introduction, the inlet may be sealed (until removal of the storage device).

In a preferred embodiment, the storage device is reusable as storage device. This means that, after use as storage device, and after subsequent removal of $CO_2$ from the storage material, i.e. regeneration of the storage material, the storage device may be used again as storage device (in the method of the invention).

Retrieval of the stored $CO_2$ may be performed with a retrieval method such as exposing the storage material to an acid and/or to heat, as described above. In an embodiment, the stored $CO_2$ from the storage device is retrieved by applying an acid to the solid based $CO_2$ storage material. The acid, such as nitric acid, may react with the storage material and form $CO_2$, i.e. release the captured $CO_2$. The released $CO_2$ can be directly conveyed to the analysis device, or it can be collected in a vial or bag, and then conveyed to the analysis site.

In another embodiment, the stored $CO_2$ from the storage device is retrieved by applying heat to the loaded storage material. In this way, the storage material (adsorbent) is desorbed. Thermal desorption can be performed, for example, by introducing the storage material or even the storage device into a heating device capable of heating to temperatures of e.g. 100-600, in particular 100-200 or 200-400° C., depending on the storage material, and carrying the desorbed $CO_2$ to the analysis device through an appropriate outlet of the heating device, and suitable gas lines. In this way, the desorbed storage material is regenerated and can then be reused for further sampling. The reversible release of $CO_2$ from the storage material results in a storage material which can be regenerated and reused. The storage material will thus not be removed from the storage device (especially a cartridge) and can be used multiple times. Heating can advantageously be achieved by means of a heating element which can be provided in the storage device, or on the sampling device or the analysis device.

Retrieval of the sampled $CO_2$ will in general be performed at the analysis site. It is to be noted that in a proportional sampling mode, the total amount of stored $CO_2$ should be released from the storage device and assayed, in order to account for variations in the $CO_2$ composition during the sampling period.

Hence, in this way the invention allows a method including sampling $CO_2$ from the flue gas stream of an incineration furnace or other $CO_2$-producing installation and storing $CO_2$ from the flue gas stream in a storage device over a certain period of time. The period of sampling time and the sampling mode are selected in such a way that the sampled $CO_2$ is representative of the composition of the flue gas stream over time. The sampling mode and period are also determined by the sensitivity and accuracy of the $^{14}C$ analysis method used. The sampling period can be as short as one minute up to a few hours, or e.g. from 1 hour up to 8 weeks or more, or from 1 day to 2 weeks or in particular in the range of 2-8 weeks, such as a month.

The $^{14}C$ determination will generally be performed at a laboratory which is situated at a distance from the sampling site. The storage device can be removed at regular intervals and replaced with another storage device, with the first sampling container being taken to a $^{14}C$-determining device.

The invention may thus allow a reliable analysis of the $^{14}C$ content remote from the incineration furnace. Herein, it is referred to an analysis site, which may be at the site of the plant itself, but may also be more remote, for instance a specialised laboratory (possibly in another country). Hence, a reliable medium for storage is especially desired. Based on the $^{14}C$ analysis, the ratio of biomass-derived and fossil-derived $CO_2$ may be determined.

In a further aspect, the invention also provides an incineration furnace comprising a sampling device arranged to sample $CO_2$ from a flue gas stream of the incineration furnace and arranged to store $CO_2$ from the flue gas stream in a storage device comprised by the sampling device, wherein the storage device comprises a solid based $CO_2$ storage material. Embodiments described above in relation to the method, the incineration furnace, the sampling device and the storage device also apply for the incineration furnace per se.

In yet a further aspect, the invention further provides a sampling device arranged to sample $CO_2$ from a flue gas stream of an incineration furnace and arranged to store $CO_2$ from the flue gas stream in a storage device comprised by the sampling device, wherein the storage device comprises a solid based $CO_2$ storage material. Especially, the storage device is a cartridge. Embodiments described above in relation to the method, the incineration furnace, the sampling device and the storage device also apply for the sampling device and storage device per se.

Thus, the invention also pertains to a storage device containing a solid $CO_2$ storage material, and comprising a sealable gas inlet and a sealable gas outlet. The storage material is preferably alumina-based or silica-based as described above. The storage device is advantageously a cartridge allowing easy and repeated mounting in and detaching from the sampling device, as well as in and from an analysis device. The storage device (cartridge) will typically comprise a solid housing, made e.g. of a metal or synthetic material. It may have any shape, such as box-like, rectangular etc., and the inlet and outlet are preferably provided at opposite ends of the storage device.

The storage device may be equipped with heating means for removal of $CO_2$ during regeneration. The heating means is preferably an electrical heating means, and may be arranged at the outside of the storage device or be integrated in the storage device, or be a unit which fits in and can be inserted into the storage device. The heating means is capable of heating the storage material to a temperature where complete desorption of $CO_2$ is achieved.

In a specific and advantageous embodiment, the cartridge is equipped with a data carrier, such as a tag, containing data which are collected during sampling and which are relevant for the assay procedure. Such data may include total flow, sample flow and time-dependent flow data, temperature, emission and authorisation data, and the like, data for controlling the handling of the storage and sampling device, such as sampling period, proportional sampling, and/or regeneration regimen including heating temperatures and regeneration times. The data can be loaded onto the data carrier by connection to sensors provided in the flue gas exhaust or the sampling device and/or can be preloaded of fixed (or sampling-dependent) data. The carrier (tag) is preferably bound to the cartridge in an inseparable manner, to secure certification of data and results The presence of the (loaded) data carrier allows the device to be analysed and processed without the need for transferring further instructions or skills to the operator performing the analysis.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EMBODIMENTS

Figure 1:
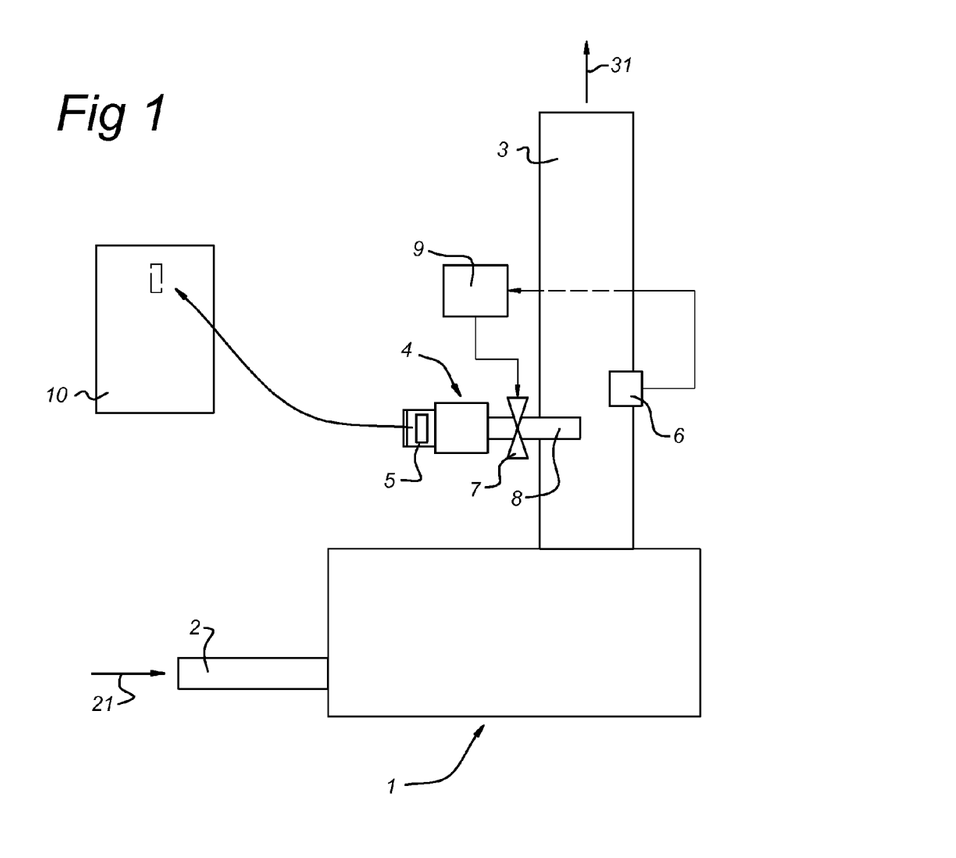
FIG. 1 schematically depicts an embodiment of an incineration furnace.

FIG. 1 schematically depicts an embodiment of the incineration furnace 1, in combination with an analysis site 10. The incineration furnace 1 comprises an inlet 2 for fuel 21.

The incineration furnace is provided with a chimney or incineration furnace outlet 3 (for the flue gas 31). The chimney contains a sampling device 4 (for sampling flue gas) and a mass flow meter 6. The sampling device comprises an sampling device inlet 8 in which a valve 7 and a sample container 5, which is further referred to as storage device 5, are arranged.

At a distance from the waste incineration furnace 1, a sample-determining device or analysis site, denoted overall by reference numeral 10, may be provided. The latter may, for example, be situated in a laboratory and is capable of determining $^{14}C$ by means of for instance the liquid scintillation method. Analysis may be performed according to ASTM D 7459-08, ASTM D 6866-08 or EN 15440 or other suitable method.

A valve control 9 may be present which may control opening and closing of the valve 7 based on the signal originating from the mass flow meter 6.

The above-described device may function as follows:

When burning fuel in the incineration furnace 1, a sample is taken continually or in any other intermittent way and placed in storage device 5. Storage device 5 is periodically replaced and the sample obtained using storage device 5 is analysed for $^{14}C$ at analysis site 10. Depending on the amount of gas which flows through the chimney 3, and which is determined by the mass flow meter, the shut-off valve 7 is preferably opened proportionally, based on the mass flow data collected by flow meter 6. That is to say, when a large amount of flue gas flows through, a large amount of material passes through the sampling device inlet 8. As a result of this proportional method, it is possible to obtain very accurate measurement results. This is particularly important when the amount of gas which flows through the incineration furnace outlet 3 varies.

Depending on the application, either the fossil carbon content or the non-fossil carbon content, or both, may be determined.

Figure 2:
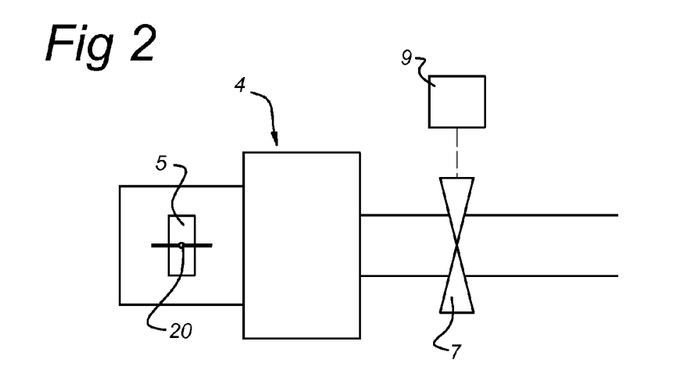
FIG. 2 schematically depicts an embodiment of the sampling device.

FIG. 2 schematically depicts in more detail an embodiment of the sampling device 4, wherein in an embodiment the storage device 5 is sealed by a seal 20. Hence, unauthorised removal or disturbance of the storage device 5 may be prevented or observed based (on the status of) the seal.

Figure 3A:
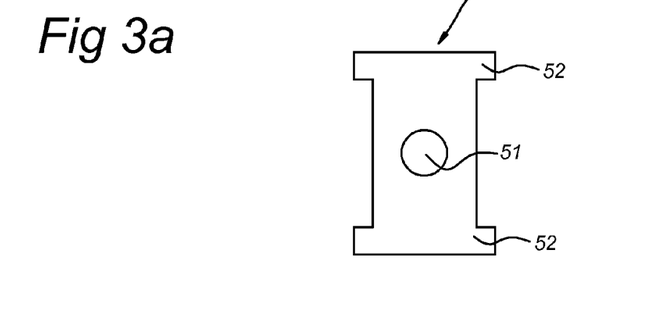
FIGS. 3a-3b schematically depict an embodiment of the storage device.
Figures 3B, 4:
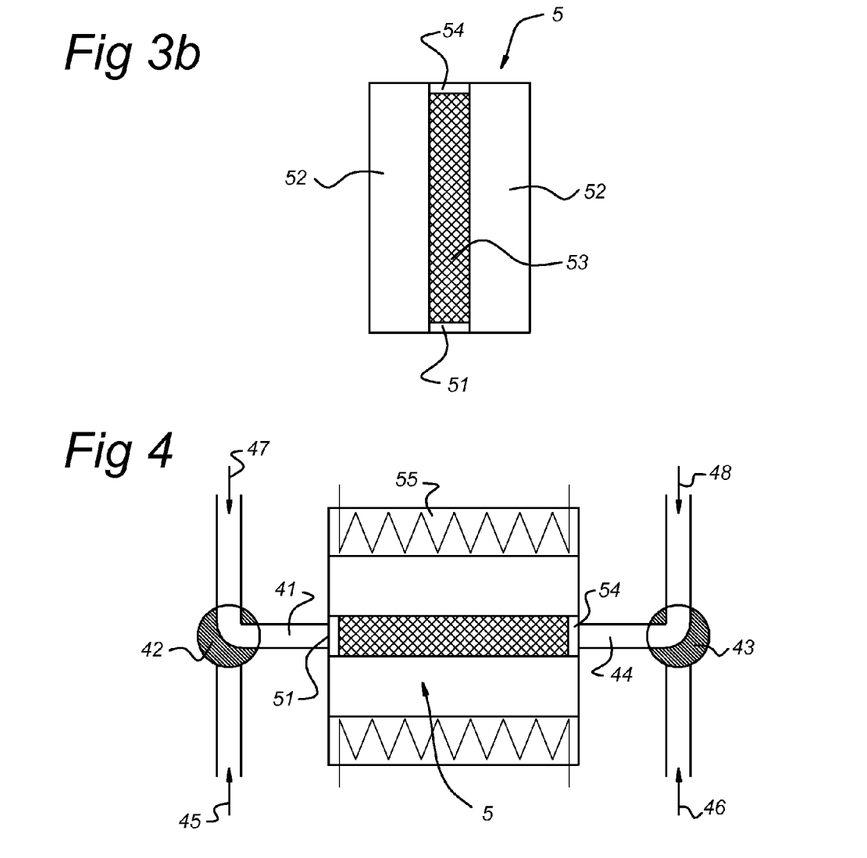
FIGS. 4 schematically depicts another embodiment of the storage device.

FIGS. 3a and 3b schematically depict an embodiment of the storage device 5 with inlet 51 for the sampled waste gas and with guiding and holding means 52, which may be used to introduce into and hold in the storage device 5 in the sampling device 4, as well as retrieving from the sampling device 4. The sampling device 4 may thus further comprise means for facilitating introduction and holding the storage device 5. Further, solid material 53, such as NaOH, is contained by the storage device, and may be loaded with $CO_2$ from the waste gas via inlet 51. Outlet 54 allows non-adsorbed gas, such as for instance $N_2$ and $O_2$, if present, to escape from the storage device 5. Inlet 51 and outlet 54 are preferably sealable.

FIG. 4 depicts an embodiment of a storage device wherein the storage material can be regenerated by heating. Storage device 5 is equipped with a heating element 55 for electrically heating the storage material. The heating element can be part of the storage device (depicted) or it can be detachable from the storage device or be part of the sampling device or an analysis unit (not depicted). Inlet and outlet conduits 41 and 44 connect inlet 51 and outlet 54 of the storage device to three-way valves 42 and 43, respectively. Three-way valve 42 can be selected to be fed from sample gas conduit 45 (which can be connected to the sampling inlet, not shown) or from regeneration gas conduit 47 (which can be connected to a regeneration gas source such as nitrogen, not shown). Three-way valve 43 can be selected to feed exit gas conduit 46 or analysis gas conduit 48. In the sampling mode, three-way valve 42 connects conduit 45 with inlet conduit 41 and three-way valve 43 connects outlet conduit 44 with conduit 46. Conduits 47 and 48 are shut off, and heating element 55 is turned off. Sampling gas then flows from the gas source through conduits 45 and 41, through the storage device 5 where $CO_2$ is absorbed, and then decarbonised through conduits 44 and 46 to the waste exit. In the regeneration mode, three-way valve 42 connects conduit 47 with inlet conduit 41 and three-way valve 43 connects outlet conduit 44 with conduit 48. Conduits 45 and 46 are shut off, and heating element 55 is turned on. Regeneration gas, e.g. nitrogen, then flows from the regeneration gas source through conduits 47 and 41, through the heated storage device 5 where $CO_2$ is desorbed, and then loaded with $CO_2$ through conduits 44 and 48 to the analysis unit, or to a container, such as a sealable vial or bag (not shown) for analysis of the $^{14}C$ of the $CO_2$. The heating temperature depends on the storage material and can e.g. be between 100 and 400° C.

Instead of three-way systems 42, 45, 47 and 43, 46, 48 being part of or being connected with the sampling device, as described above, the sampling device may just provide inlet and outlet conduits 41 and 44, which are sealable. These may be connected to the feed and discharge lines of the sampling device in the sampling mode, and—after transport to the analysis site—to the regeneration gas feed and analysis lines of the analysis unit in the regeneration mode.

As a further alternative, not shown, the three-way valve 42 and conduit 47 are absent, and sample gas is also supplied during the regeneration mode to act as regeneration gas, while the storage device is heated.

Hence, the invention allows a determination of the relative amounts of biomass-derived and fossil-derived $CO_2$ in the flue gas stream of an incinerator. Further, the invention allows determination of the relationship between fossil and non-fossil energy carriers in a fuel (mixture) by determining the ratio of biomass-derived and fossil-derived $CO_2$ in a flue gas stream of an incineration furnace wherein the fuel (mixture) is combusted, and deriving thereof the relationship between fossil and non-fossil energy carriers in the fuel (mixture) (combusted by the incineration furnace).

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method for sampling and analysing $CO_2$ from a $CO_2$-containing flue gas stream, comprising:
   a. providing a sampling device having a gas inlet and a gas outlet,
   b. introducing a storage device into the sampling device, by means of a sealable inlet and outlet, the storage device comprising a solid $CO_2$ storage material comprising a metal hydroxide on a silica or alumina carrier;
   c. passing gas from the flue gas stream through the storage device during a sampling period, wherein the amount of flue gas passed through the storage device is proportional to the total flow of the flue gas stream;
   d. detaching the storage device from the sampling device after said sampling period and transporting it to an analysis site;
   e. retrieving the $CO_2$ from the storage device at the analysis site by dissolving the storage material and subsequently determining the $^{14}C$ content of the retrieved $CO_2$; and
   f. re-using the storage device for introduction into the sampling device in step (b).

2. The method according to claim 1, wherein the flue gas stream is a flue gas stream of an incinerator furnace.

3. The method according to claim 1, wherein the storage device further comprises a data carrier for carrying sampling data.

4. The method according to claim 1, wherein the storage device is a cartridge.

5. The method according to claim 1, wherein the solid storage material is based on silica.

6. The method according to claim 1, wherein the solid based $CO_2$ storage material comprises one or more materials selected from NaOH, KOH, LiOH, $Mg(OH)_2$, $Ca(OH)_2$, $Sr(OH)_2$, and $Ba(OH)_2$.

7. The method according to claim 1, wherein the sampling period is a period of up to 8 weeks.

8. The method according to claim 7, wherein the sampling period is 2-8 weeks.

* * * * *